United States Patent
Merten et al.

(10) Patent No.: US 8,067,617 B2
(45) Date of Patent: Nov. 29, 2011

(54) INDOLINONE DERIVATIVES AND PROCESS FOR THEIR MANUFACTURE

(75) Inventors: Joern Merten, Gau Algesheim (DE); Svenja Renner, Eckenroth (DE); Carsten Reichel, Rheinboellen (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 12/745,788

(22) PCT Filed: Dec. 2, 2008

(86) PCT No.: PCT/EP2008/066581
§ 371 (c)(1),
(2), (4) Date: Aug. 25, 2010

(87) PCT Pub. No.: WO2009/071524
PCT Pub. Date: Jun. 11, 2009

(65) Prior Publication Data
US 2010/0311985 A1 Dec. 9, 2010

(30) Foreign Application Priority Data
Dec. 3, 2007 (EP) ..................... 07122123

(51) Int. Cl.
*C07D 209/34* (2006.01)
(52) U.S. Cl. ...................................... 548/469
(58) Field of Classification Search ............ 548/469
See application file for complete search history.

(56) References Cited

U.S. PATENT DOCUMENTS
6,469,181 B1 10/2002 Gruber et al.
2003/0092756 A1 5/2003 Roth et al.

FOREIGN PATENT DOCUMENTS
CA 2342622 A1 4/2004
CA 2498781 A1 4/2004
WO 9623770 A1 8/1996
WO 0018734 A1 4/2000
WO 02081445 A1 10/2002
WO 2004026829 A2 4/2004

OTHER PUBLICATIONS

International Search Report, Form PCT/ISA/210, for corresponding PCT/EP2008/066580, Date of mailing Aug. 10, 2009.
T. W. Greene et al.; Protective Groups in Organic Synthesis; pp. 550-556; John Wiley & Sons; XP002538466; New York.

*Primary Examiner* — Shawquia Young
(74) *Attorney, Agent, or Firm* — Michael P. Morris; Alan R. Stempel

(57) ABSTRACT

The present invention relates to specific indolinone derivatives, namely the compounds of formula, in which $R^1$ represents an hydrogen atom or a group, and $R^2$ and $R^3$ each represent an hydrogen atom or $R^2$ and $R^3$ taken together represent a group, with the proviso that when $R^1$ represents an hydrogen atom $R^2$ and $R^3$ taken together represent a group, and to a process for their manufacture.

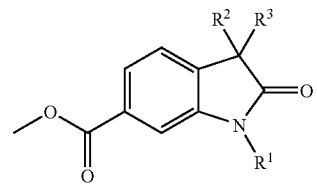

(I)

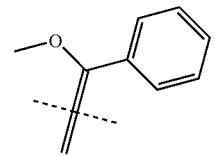

(II)

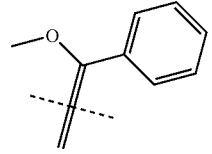

(III)

10 Claims, No Drawings

INDOLINONE DERIVATIVES AND PROCESS FOR THEIR MANUFACTURE

The present invention relates to specific indolinone derivatives, namely the compounds of formula

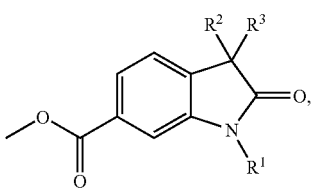

in which $R^1$ represents an hydrogen atom or a Cl—$CH_2$—CO-group, and $R^2$ and $R^3$ each represent an hydrogen atom or $R^2$ and $R^3$ taken together represent a

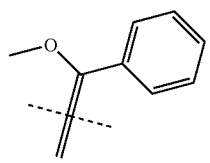

group,
with the proviso that when $R^1$ represents an hydrogen atom $R^2$ and $R^3$ taken together represent a

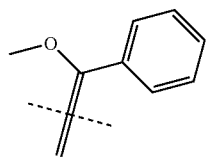

group,
and to a process for their manufacture.

The above mentioned indolinone derivatives are useful intermediates for the synthesis of drug substances, such as those disclosed for example in the following patent applications: WO 01/027081, WO 04/013099, WO 04/017948, WO 04/096224 and WO 06/067165. These patent applications disclose drug substances and the use of these drug substances or of a pharmaceutically acceptable thereof in a pharmaceutical composition to treat oncological or non-oncological diseases via inhibition of the proliferation of target cells, alone or in combination with further therapeutic agents. The mechanism of action by which the proliferation of the target cells occurs is essentially a mechanism of inhibition of several tyrosine kinase receptors, and especially an inhibition of the vascular endothelial growth factor receptor (VEGFR).

Although the above-mentioned patent applications already describe a process to manufacture the drug substances, an object of the present invention is a new and improved process for the manufacture of intermediates useful for the synthesis of said drug substances. Hence, the process in accordance with the present invention presents amongst others the following remarkable advantages when compared to the processes already described in the prior art.

A first advantage is the higher overall yield which can be obtained via the new and improved process. This higher overall yield represents an improvement in the overall efficiency of the process. This implies also an economic advantage.

A second advantage is that the new and improved process in accordance with the present invention is more friendly towards the environment than the processes already known from the prior art. This advantage is based on the fact that the process steps are conducted at higher concentrations.

A third advantage which can be pointed out is the large scale production appropriateness of the new and improved process in accordance with the present invention. This appropriateness is characterized by the presence of robust reaction steps, i.e. reaction steps which are less sensitive to the inputs.

These advantages ensure the required high purity of the active pharmaceutical active ingredient.

The process in accordance with the present invention is shown in the following General Synthesis Scheme 1.

General Synthesis Scheme 1

Synthesis of 6-methoxycarbonyl-2 oxindole

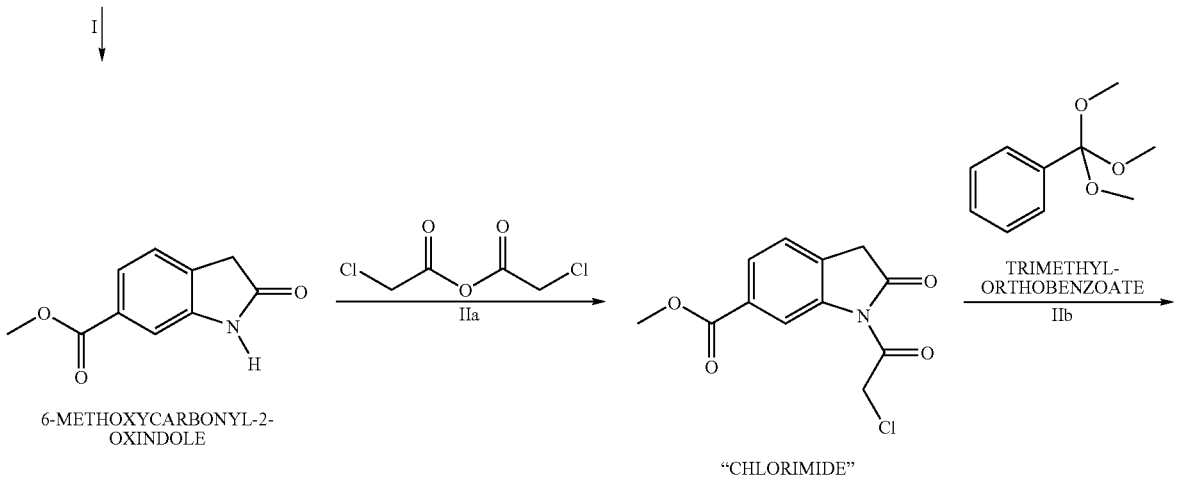

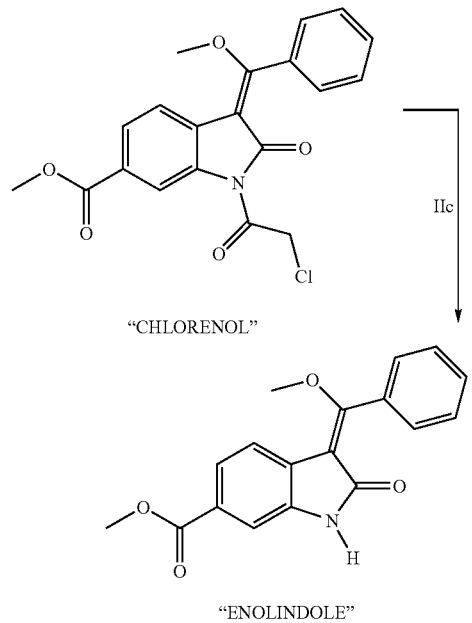

"CHLORENOL"

↓ IIc

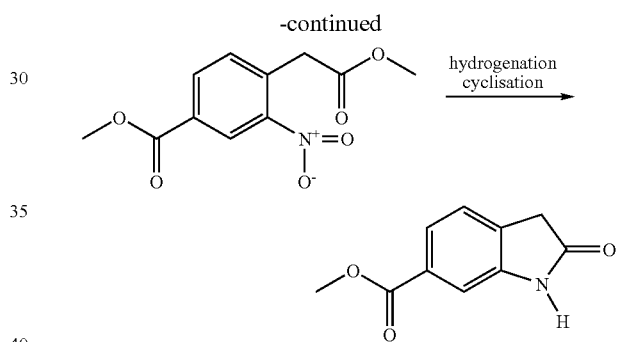

"ENOLINDOLE"

The following nomenclature is used throughout the present invention.

| Custom name used in present patent application | Corresponding IUPAC name |
|---|---|
| "CHLORIMIDE" | methyl 1-(chloroacetyl)-2-oxoindoline-6-carboxylate |
| "CHLORENOL" (E or Z isomer) | methyl 1-(chloroacetyl)-3-[methoxy(phenyl)methylene]-2-oxoindoline-6-carboxylate |
| "ENOLINDOLE" (E or Z isomer) | methyl 3-[methoxy(phenyl)methylene]-2-oxoindoline-6-carboxylate |

Thus, in accordance with the present invention, the process comprises the following steps.

I. Synthesis of the 6-methoxycarbonyl-2-oxindole

The 6-methoxycarbonyl-2-oxindole may be synthesized in accordance with the processes shown in following synthesis schemes A or B. These processes have already been described in the prior art.

Synthesis scheme A

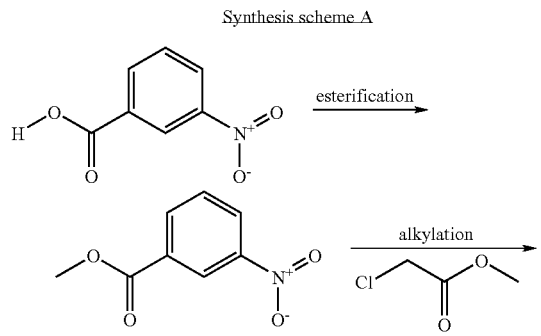

Hence, the 6-methoxycarbonyl-2-oxindole is obtainable by a three-step procedure consisting of an esterification of 3-nitro-benzoic acid, followed by an electrophilic substitution using chloroacetic acid methyl ester, leading to 4-methoxycarbonylmethyl-3-nitro-benzoic acid methyl ester, and to a final hydrogenation-intramolecular amidation sequence.

Synthesis scheme B

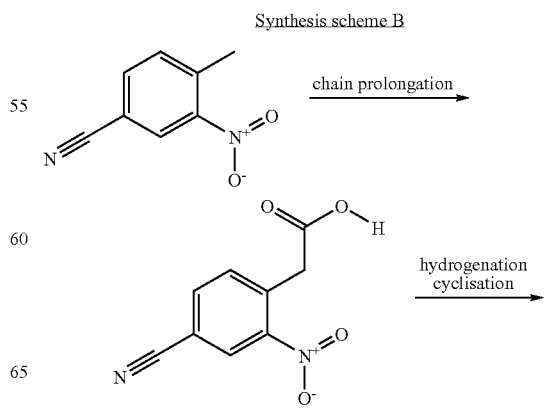

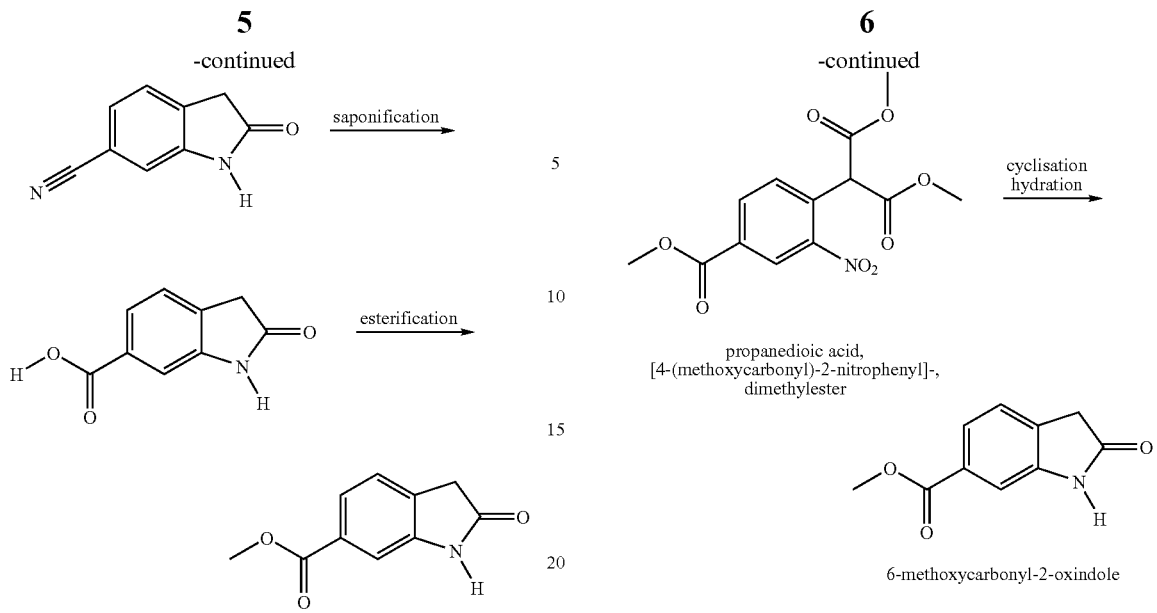

The 6-methoxycarbonyl-2-oxindole is also obtainable by the above four-step procedure. Starting with the chain prolongation of 4-methyl-3-nitro-benzonitrile and reductive cyclisation of the resulting (4-cyano-2-nitrophenyl)acetic acid to the oxindole scaffold, the synthesis is concluded by the saponification of the nitrile group and the subsequent esterification of the carboxylic acid functionality.

Alternatively, the 6-methoxycarbonyl-2-oxindole may also be synthesized in accordance with the process to synthesize 2-oxindoles described in U.S. Pat. No. 6,469,181.

Alternatively, the 6-methoxycarbonyl-2-oxindole may be synthesized in accordance with the process shown in the following synthesis scheme C.

The steps of this synthesis scheme C, which is also an object of the present invention, will be further described in the following experimental Example 1, which shall not be construed as a limitation of the present invention.

IIa. Reaction of the 6-methoxycarbonyl-2-oxindole with Chloroacetic Anhydride to Obtain the "Chlorimide" (Methyl 1-(chloroacetyl)-2-oxoindoline-6-carboxylate)

The reaction of 6-methoxycarbonyl-2-oxindole with chloroacetic anhydride or another appropriately activated chloroacetic acid derivative, e.g. chloroacetyl chloride, is preferably carried out in a high boiling and aprotic solvent, for instance toluene, xylene or butyl acetate, at a temperature of about 80° C. to about 130° C.

The crystallisation is initiated by addition of a non-polar solvent, for instance cyclohexane or methyl cyclohexane, at a temperature of about 80° C. to about 100° C., and completed at a temperature of about −5° C. to room temperature. The solid is collected, washed, preferably with polar solvents such as alcohols, most preferably methanol, and dried, to generate the "chlorimide" compound.

The alkylating agents such as chloroacetyl chloride or chloroacetic anhydride may be purchased from different sources. A supplier of large amounts of chloroacetic anhydride is, for example, SF-Chem (Switzerland).

The above reaction step IIa and the product of the reaction, i.e. the "chlorimide" (methyl 1-(chloroacetyl)-2-oxoindoline-6-carboxylate), are also an object of the present invention.

IIb. Reaction of the "Chlorimide" with Trimethylorthobenzoate to Obtain the "Chlorenol" (Methyl 1-(chloroacetyl)-3-[methoxy(phenyl)methylene]-2-oxoindoline-6-carboxylate)

The reaction of the methyl 1-(chloroacetyl)-2-oxoindoline-6-carboxylate with trimethylorthobenzoate is carried out in a high boiling and aprotic solvent such as butyl acetate, N,N-dimethylformamide, xylene or preferably toluene, at temperatures of about 100° C. to about 140° C. The reaction is mediated by methanol scavengers such as acetic anhydride. In the course of the reaction, volatile parts can be distilled off with or without replacement of the removed parts by the reaction solvent. The crystallisation is finished at ambient temperature to about −10° C. The solid is collected and washed, preferably with solvents such as toluene, xylene and/or ethyl acetate. After drying, the "chlorenol" compound is obtained.

Acetic anhydride may be purchased from different sources. Trimethylorthobenzoate may be purchased from AMI Drugs & Speciality Chemicals India Inc.

The above reaction step IIb and the product of the reaction, i.e. the "chlorenol" (methyl 1-(chloroacetyl)-3-[methoxy (phenyl)methylene]-2-oxoindoline-6-carboxylate), are also an object of the present invention.

IIc. Reaction of the "Chlorenol" with Bases to Obtain the "Enolindole" (methyl-3-[methoxy(phenyl)methylene]-2-oxoindoline-6-carboxylate)

The base catalyzed dechloroacetylation of methyl-1-(chloroacetyl)-3-[methoxy(phenyl)methylene]-2-oxoindoline-6-carboxylate is carried out in protic solvents such as alcohols, e.g. isopropanol or preferably methanol, at temperatures of about 70° C. to ambient temperature. Inorganic bases such as alkali hydroxides or organic bases such as sodium methoxide may be used as catalysts. The crystallisation is finished at ambient temperature to about −10° C. The solid is collected and washed, preferably with alcohols, most preferably methanol. After drying, the "enolindole" compound is obtained.

The above reaction step IIc and the product of the reaction, i.e. the "enolindole" (methyl-3-[methoxy(phenyl)methylene]-2-oxoindoline-6-carboxylate), are also an object of the present invention.

A first object of the present invention is thus a compound of formula

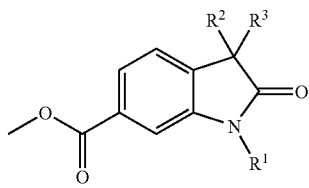

in which $R^1$ represents an hydrogen atom or a Cl—CH$_2$—CO-group, and $R^2$ and $R^3$ each represent an hydrogen atom or $R^2$ and $R^3$ taken together represent a

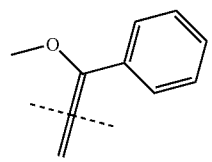

group, with the proviso that when $R^1$ represents an hydrogen atom $R^2$ and $R^3$ taken together represent a

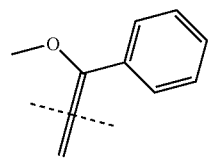

group.

A further object of the present invention is the compound of formula

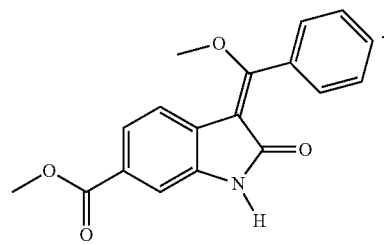

A further object of the present invention is the compound of formula

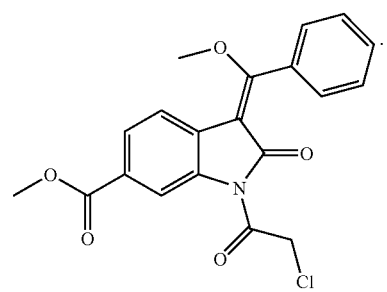

A further object of the present invention is the compound of formula

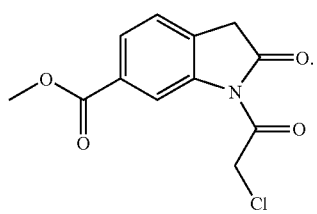

A further object of the present invention is the following process D for the manufacture of a compound of formula

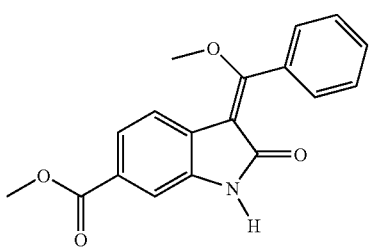

which comprises the step of base catalyzed dechloroacetylation of a compound of formula

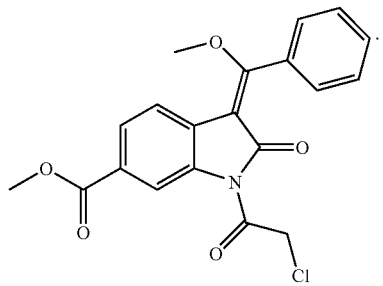

A further object of the present invention is the following process D1, based on the above process D, and in which the compound of formula

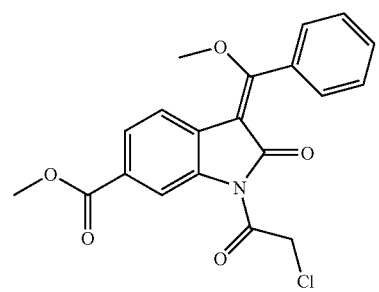

is obtained by reacting a compound of formula

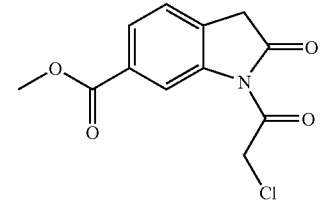

with a compound of formula

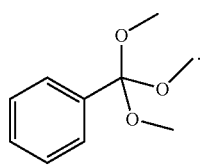

A further object of the present invention is the following process D2, based on the above process D1, and in which the compound of formula

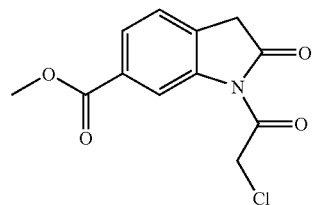

is obtained by reacting a compound of formula

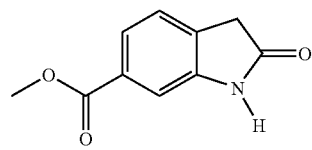

with a compound of formula

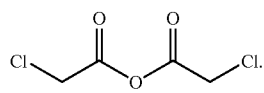

A further object of the present invention is the following process D3, based on the above processes D2, and in which the compound of formula

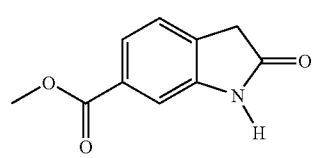

is obtained by the following steps:
(i) esterification of a compound of formula

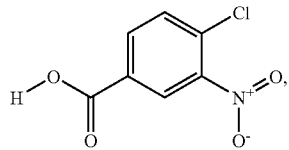

to obtain a compound of formula

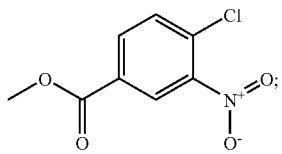

(ii) reacting the product of the reaction (i) with malonic acid dimethylester, to obtain a compound of formula

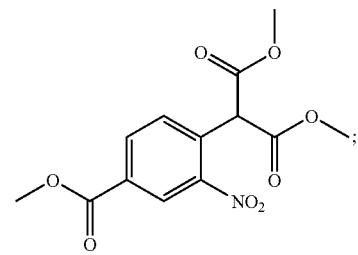

(iii) performing a cyclisation of the product of the reaction (ii) by a reaction of hydrogenation.

A further object of the present invention is a process for the manufacture of a compound of formula

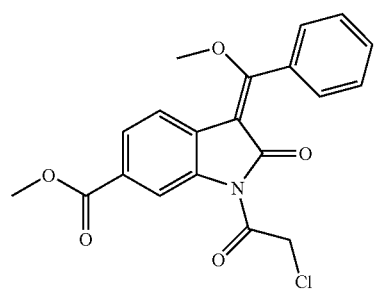

comprising the step of reacting a compound of formula

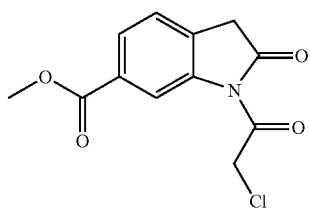

with a compound of formula

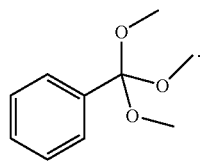

A further object of the present invention is a process for the manufacture of a compound of formula

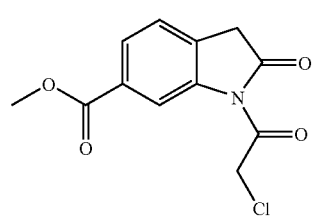

comprising the step of reacting a compound of formula

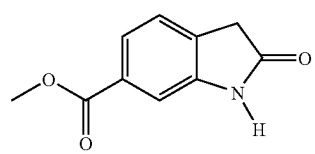

with a compound of formula

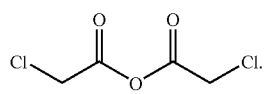

The present invention will be described in more details in the following by way of examples, which are illustrative of further embodiments and shall not construe a limitation of the invention.

In the following examples, the synthesis of the drug substance 3-Z-[1-(4-(N-((4-methyl-piperazin-1-yl)-methylcarbonyl)-N-methyl-amino)-anilino)-1-phenyl-methylene]-6-methoxycarbonyl-2-indolinone, disclosed in WO 01/027081, WO 04/013099, WO 04/017948, WO 04/096224 and WO 06/067165, is described.

This synthesis is performed in accordance with the following General Synthesis Scheme 2.

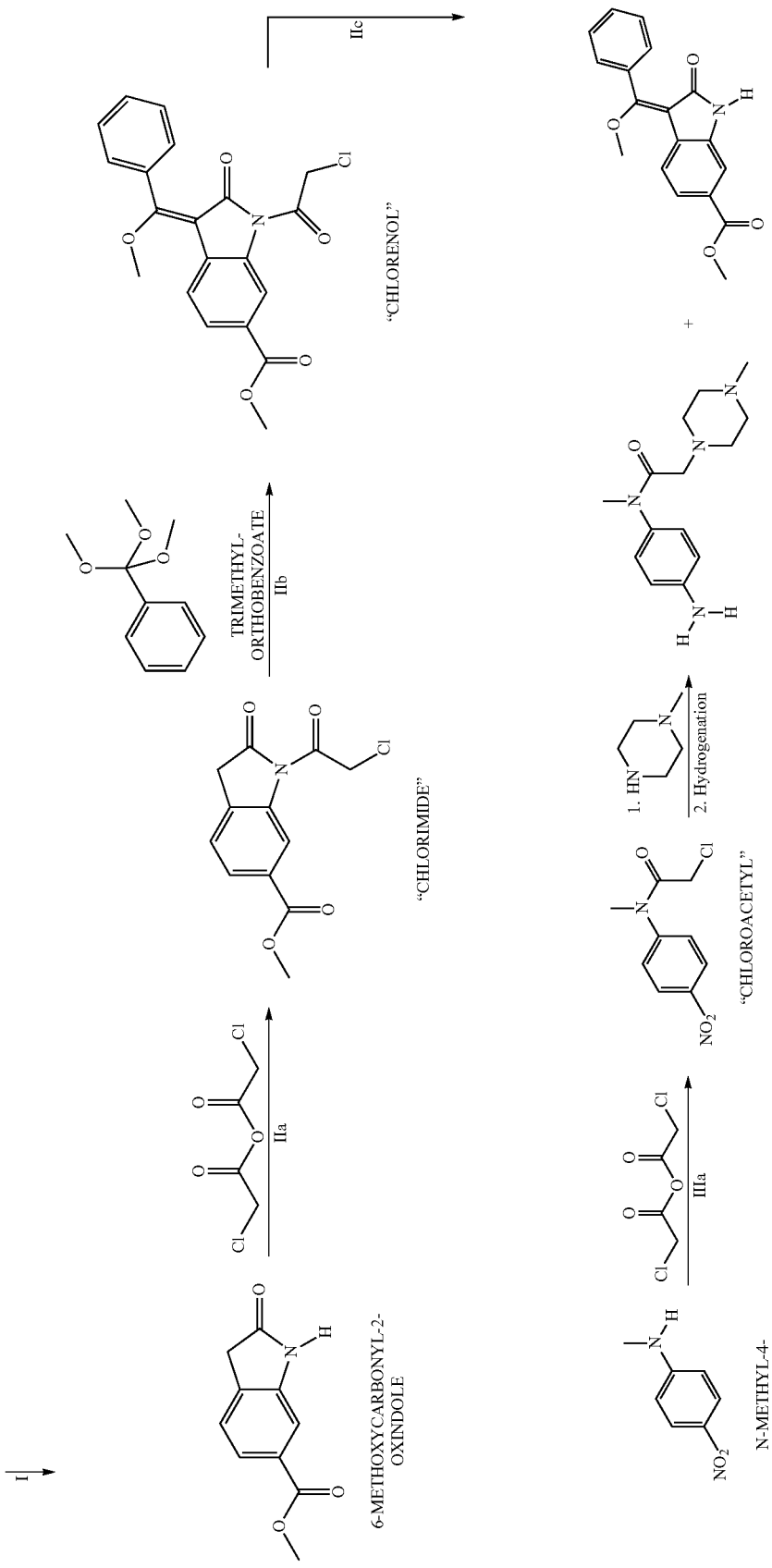

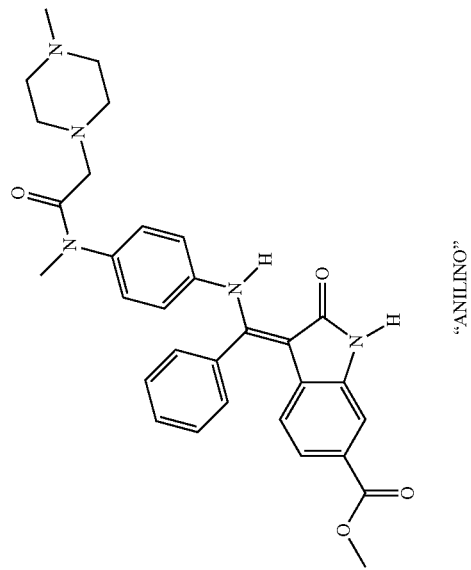

In the above General Synthesis Scheme 2 and in the following Examples, the following nomenclature is used.

| Custom name used in present patent application | Corresponding chemical name used in present patent application | Corresponding IUPAC name |
|---|---|---|
| "CHLORIMIDE" | | methyl 1-(chloroacetyl)-2-oxoindoline-6-carboxylate |
| "CHLORENOL" (E or Z isomer) | | methyl 1-(chloroacetyl)-3-[methoxy(phenyl)methylene]-2-oxoindoline-6-carboxylate |
| "CHLOROACETYL" | chloracetyl-N-methyl-4-nitroaniline | N-(4-nitroanilino)-N-methyl-2-chloro-acetamide |
| "NITROANILINE" | | N-(4-nitrophenyl)-N-methyl-2-(4-methylpiperazin-1-yl)acetamide |
| "ANILINE" | | N-(4-aminophenyl)-N-methyl-2-(4-methylpiperazin-1-yl)acetamide |
| "ENOLINDOLE" (E or Z isomer) | | methyl 3-[methoxy(phenyl)methylene]-2-oxoindoline-6-carboxylate |
| "ANILINO" | 3-Z-[1-(4-(N-((4-methyl-piperazin-1-yl)-methylcarbonyl)-N-methyl-amino)-anilino)-1-phenyl-methylene]-6-methoxycarbonyl-2-indolinone | methyl (3Z)-3-[[(4-{methyl[(4-methylpiperazin-1-yl)acetyl]amino}phenyl)amino](phenyl)methylene]-2-oxoindoline-6-carboxylate |

EXAMPLE 1

Synthesis of the 6-methoxycarbonyl-2-oxindole in Accordance with the Process Shown in Synthesis Scheme C Synthesis of Benzoic Acid, 4-chloro-3-nitro-, Methylester 20 kg of 4-chloro-3-nitro-benzoic acid (99.22 mol) is suspended in 76 L methanol. 5.9 kg thionylchloride (49.62 mol) is added within 15 minutes and refluxed for about 3 hours. After cooling to about 5° C., the product is isolated by centrifugation and drying at 45° C.
Yield: 19.0 kg (88.8% of theoretical amount)
Purity (HPLC): 99.8%

Synthesis of Propanedioic Acid, [4-(methoxycarbonyl)-2-nitrophenyl]-, Dimethylester 12.87 kg of malonic acid, dimethylester (97.41 mol) is added to a hot solution (75° C.) of 10.73 kg sodium-tert.amylate (97.41 mol) in 35 L 1-methyl-2-pyrrolidinone (NMP). A solution of 10 kg benzoic acid, 4-chloro-3-nitro-, methylester (46.38 mol) in 25 L 1-methyl-2-pyrrolidinone is added at 75° C. After stirring for 1.5 hours at about 75° C. and cooling to 20° C., the mixture is acidified with 100 L diluted hydrochloric acid to pH 1. After stirring for 1.5 hours at about 5° C., the product is isolated by centrifugation and drying at 40° C.
Yield: 13.78 kg (95.4% of theoretical amount)
Purity (HPLC): 99.9%

Synthesis of 6-methoxycarbonyl-2-oxindole

A solution of 13 kg propanedioic acid, [4-(methoxycarbonyl)-2-nitrophenyl]-, dimethylester (41.77 mol) in 88 L acetic acid is hydrogenated at 45° C. and under 40-50 psi in the presence of 1.3 kg Pd/C 10%. After standstill of the hydrogenation, the reaction is heated up to 115° C. for 2 hours. The catalyst is filtered off and 180 L water is added at about 50° C. The product is isolated after cooling to 5° C., centrifugation and drying at 50° C.
Yield: 6.96 kg (87.2% of theoretical amount)
Purity (HPLC): 99.8%

EXAMPLE 2

Synthesis of the "Chlorimide" (methyl-1-(chloro-acetyl)-2-oxoindoline-6-carboxylate)

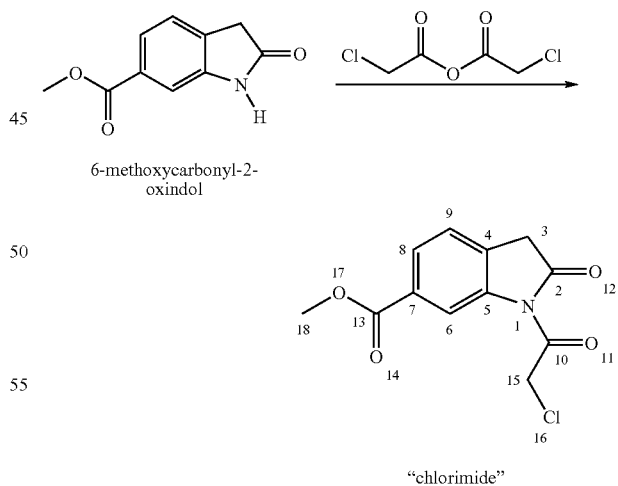

"chlorimide"

Method 1

6-methoxycarbonyl-2-oxindole (400 g; 2.071 mol) is suspended in toluene (1200 ml) at room temperature. Chloroacetic anhydride (540 g; 3.095 mol) is added to this suspension. The mixture is heated to reflux for 3 h, then cooled to 80° C. and methyl cyclohexane (600 ml) is added within 30 min. The resulting suspension is further cooled down to room temperature within 60 min. The mother liquor is separated and the solid is washed with ice cold methanol (400 ml). The crystals are dried to afford 515.5 g (93.5%) of the "chlorimide" compound as a white solid. $^1$H-NMR (500 MHz, DMSO-$d_6$) δ: 8.66 (s, 1 H, 6-H); 7.86 (d, J=8.3 Hz, 1 H, 8-H); 7.52 (d, J=8.3 Hz, 1 H, 9-H); 4.98 (s, 1 H, 15-$H_2$); 3.95 (s, 1 H, 18-$H_3$); 3.88 (s, 1 H, 3-$H_2$). $^{13}$C-NMR (126 MHz, DMSO-$d_6$) δ: 174.7 (C-2); 36.0 (C-3); 131.0 (C-4); 140.8 (C-5); 115.7 (C-6); 128.9 (C-7); 126.1 (C-8); 124.6 (C-9); 166.6 (C-10); 165.8 (C-13); 46.1 (C-15); 52.3 (C-18). MS: m/z 268 (M+H)$^+$. Anal. calcd. for $C_{12}H_{10}ClNO_4$: C, 53.85; H, 3.77; Cl, 13.25; N, 5.23. Found: C, 52.18; H, 3.64; Cl, 12.89; N, 5.00.

Method 2

6-methoxycarbonyl-2-oxindole (10 g; 0.052 mol) is suspended in n-butyl acetate (25 ml) at room temperature. To this suspension a solution of chloroacetic anhydride (12.8 g; 0.037 mol) in n-butyl acetate (25 ml) is added within 3 min. The mixture is heated to reflux for 2 h, then cooled to 85° C. and methyl cyclohexane (20 ml) is added. The resulting suspension is further cooled down to room temperature and stirred for an additional 2 h. The mother liquor is separated and the solid is washed with methanol (400 ml) at ambient temperature. The crystals are dried to afford 12.7 g (91.5%) of the "chlorimide" compound as a slightly yellow solid.

EXAMPLE 3

Synthesis of the "Chlorenol" (methyl-1-(chloro-acetyl)-3-[methoxy(phenyl)methylene]-2-oxoindoline-6-carboxylate)

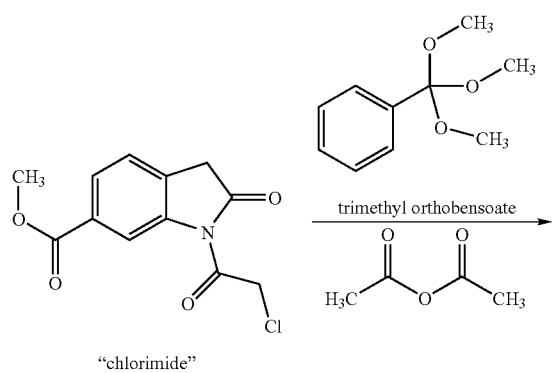

"chlorimide"

Method 1

Methyl-1-(chloroacetyl)-2-oxoindoline-6-carboxylate (12.0 g; 0.045 mol) is suspended in toluene (60 ml) at ambient temperature. Acetic anhydride (16.2 g; 0.157 mol) is added to this suspension. The mixture is heated to not less than 104° C. and trimethyl orthobenzoate (20.0 g; 0.108 mol) is added within 60 min. During the addition period and subsequent stirring at the same temperature for 3 h, volatile parts of the reaction mixture are distilled off. The concentration of the reaction mixture is kept constant by replacement of the distilled part by toluene (40 ml). The mixture is cooled down to 5° C., stirred for an additional 1 h and filtrated. The solid is subsequently washed with toluene (14 ml) and with a mixture of toluene (8 ml) and ethyl acetate (8 ml). After drying, 16.3 g (91.7%) of the "chlorenol" compound are isolated as slightly yellow crystals. $^1$H-NMR (500 MHz, DMSO-$d_6$) δ: 8.73 (d, J=1.5 Hz, 1 H, 6-H); 8.09 (d, J=8.0 Hz, 1 H, 9-H); 7.90 (dd, J=8.1; 1.5 Hz, 1 H, 8-H); 7.61-7.48 (m, 1 H, 21-H, 22-H, 23-H, 24-H, 25-H); 4.85 (s, 1 H, 18-$H_2$); 3.89 (s, 1 H, 27-$H_3$); 3.78 (s, 1 H, 15-$H_3$). $^{13}$C-NMR (126 MHz, DMSO-$d_6$) δ: 165.9 (C-2+C16); 103.9 (C-3); 127.4; 128.6; 130.0; 135.4 (C-4+C-5+C-7+C-20); 115.1 (C-6); 126.1 (C-8); 122.5 (C-9); 166.7 (C-10); 173.4 (C-13); 58.4 (C-15); 46.4 (C-18); 128.6 (C-21+C-22+C-24+C-25); 130.5 (C-23); 52.2 (C-27). MS: m/z 386 (M+H)$^+$. Anal. calcd. for $C_{20}H_{16}ClNO_5$: C, 62.27; H, 4.18; Cl, 9.19; N, 3.63. Found: C, 62.21; H, 4.03; Cl, 8.99; N, 3.52.

Method 2

Methyl-1-(chloroacetyl)-2-oxoindoline-6-carboxylate (12.0 g; 0.045 mol) is suspended in xylene (60 ml) at ambient temperature. Acetic anhydride (16.2 g; 0.157 mol) is added to this suspension. The mixture is heated to reflux, trimethyl orthobenzoate (20.0 g; 0.108 mol) is added within 40 min and heating is maintained for an additional 4 h. The mixture is cooled down to 0° C. and the mother liquor is separated. The solid is subsequently washed with xylene (14 ml) and a mixture of xylene (8 ml) and ethyl acetate (8 ml). After drying 14.3 g (81.0%) of the "chlorenol" compound are isolated as yellow crystals.

Method 3

Methyl-1-(chloroacetyl)-2-oxoindoline-6-carboxylate (12.0 g; 0.045 mol) is suspended in toluene (60 ml) at ambient temperature. Acetic anhydride (16.2 g; 0.157 mol) is added to this suspension. The mixture is heated to reflux, trimethyl orthobenzoate (20.0 g; 0.108 mol) is added within 40 min and heating is maintained for an additional 3 h. The mixture is cooled down to 0° C. and the mother liquor is separated. The solid is subsequently washed with toluene (14 ml) and a mixture of toluene (8 ml) and ethyl acetate (8 ml). After drying 15.3 g (87.3%) of the "chlorenol" compound are isolated as fawn crystals.

EXAMPLE 4

Synthesis of the "Enolindole" (methyl-3-[methoxy (phenyl)methylene]-2-oxoindoline-6-carboxylate)

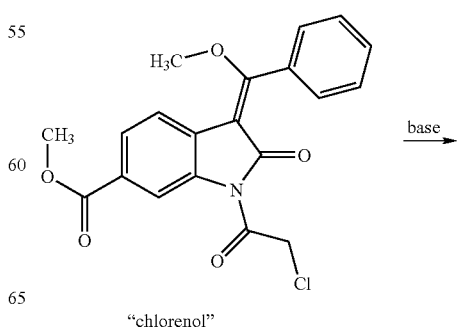

"chlorenol"

21
-continued

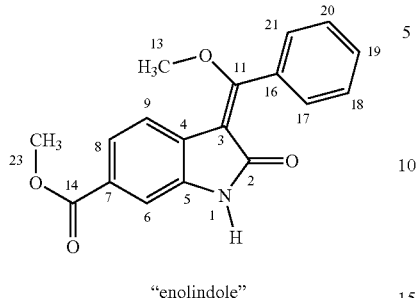

"enolindole"

Method 1

A solution of potassium hydroxide (0.41 g, 0.006 mol) in methanol (4 ml) is added at 63° C. to a suspension of methyl-1-(chloroacetyl)-3-[methoxy(phenyl)methylene]-2-oxoindoline-6-carboxylate (8.0 g; 0.020 mol) in methanol (32 ml) C. The mixture is then stirred for 30 min, cooled to 0° C. and stirring is maintained for 2 h. After filtration, the solid is washed with methanol (24 ml) and dried to afford 6.0 g (94.6%) of the "enolindole" compound as yellow crystals. $^1$H-NMR (500 MHz, CDCl$_3$) δ: 8.08 (s, 1 H, 1-H); 7.88 (d, J=7.8 Hz, 1 H, 9-H); 7.75 (m, 1 H, 8-H); 7.52-7.56 (m, 1 H, 18-H, 19-H, 20-H); 7.40-7.45 (m, 1 H, 6-H, 17-H, 21-H); 3.92 (s, 1 H, 23-H$_3$); 3.74 (s, 1 H, 13-H$_3$). $^{13}$C-NMR (126 MHz, CDCl$_3$) δ: 168.8 (C-2); 107.4 (C-3); 130.8 (C-4); 138.2 (C-5); 109.4 (C-6); 128.2 and 128.3 (C-7, C-16); 123.5 (C-8); 123.1 (C-9); 170.1 (C-11); 57.6 (C-13); 167.2 (C-14); 128.7 and 128.9 (C-17, C-18, C-20, C-21); 130.5 (C-19); 52.1 (C-23). MS (m/z): 310 (M+H)$^+$. Anal. calcd. for C$_{18}$H$_{15}$NO$_4$: C, 69.89; H, 4.89; N, 4.53. Found: C, 69.34; H, 4.92; N, 4.56.

Method 2

A suspension of methyl-1-(chloroacetyl)-3-[methoxy (phenyl)methylene]-2-oxoindoline-6-carboxylate (7.0 g; 0.018 mol) in methanol (28 ml) is heated to reflux. Within 3 min, a solution of sodium methoxide in methanol (0.24 g, 30 (w/w), 0.001 mol) is added to this suspension. The mixture is then stirred for 30 min, cooled to 5° C. and stirring is maintained for 2 h. After filtration, the solid is washed with methanol (9 ml) and dried to afford 5.4 g (89.7%) of the "enolindole" compound as yellow crystals.

Method 3

A suspension of methyl-1-(chloroacetyl)-3-[methoxy (phenyl)methylene]-2-oxoindoline-6-carboxylate (8.0 g; 0.021 mol) in methanol (32 ml) is heated to reflux. A solution of sodium methoxide in methanol (0.74 g, 30% (w/w), 0.004 mol), further diluted with methanol (4 ml), is added dropwise to this suspension. The mixture is then stirred for 90 min, cooled to 0° C. and stirring is maintained for 2 h. After filtration, the solid is washed with methanol (24 ml) and dried to afford 5.9 g (91.2%) of the "enolindole" compound as yellow crystals.

22
EXAMPLE 5

Synthesis of the "Chloroacetyl" (N-(4-nitroanilino)-N-methyl-2-chloro-acetamide)

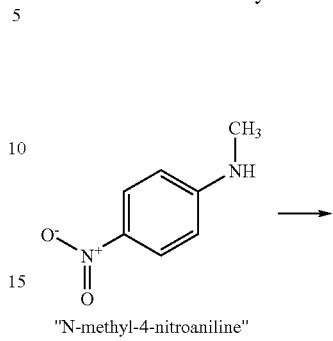

"N-methyl-4-nitroaniline"

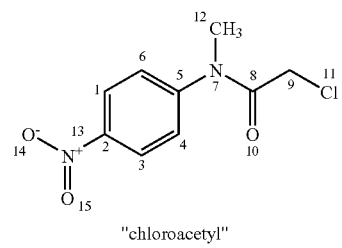

"chloroacetyl"

Method 1

A suspension of N-methyl-4-nitroaniline (140 g; 0.920 mol) in ethyl acetate (400 ml) is heated to 70° C. Within 90 min, chloro acetylchloride (114 g; 1.009 mol) is added to this suspension. The resulting solution is then refluxed for 1 h, cooled to 60° C. and methyl cyclohexane (245 ml) is added. The suspension is further cooled down to 0° C. and stirred for an additional 1 h. The reaction mixture is filtrated, washed with methyl cyclohexane (285 ml) and the precipitate is dried to afford 210.4 g (92.7%) of the "chloroacetyl" compound as white crystals. $^1$H-NMR (500 MHz, DMSO-d$_6$) δ: 8.29 (d, J=8.5 Hz, 1 H, 1-H+3-H); 7.69 (d, J=8.5 Hz, 1 H, 4-H+6-H); 4.35 (s, 1 H, 9-H$_2$); 3.33 (s, 1 H, 12-H$_3$). $^{13}$C-NMR (126 MHz, DMSO-d$_6$) δ: 124.6 (C-1+C-3); 145.6 (C-2); 127.4 (C-4+C-6); 148.6 (C-5); 165.6 (C-8); 42.7 (C-9); 37.2 (C-12). MS (m/z): 229 (M+H)$^+$. Anal. calcd. for C$_9$H$_9$ClN$_2$O$_3$: C, 47.28; H, 3.97; N, 12.25. Found: C, 47.26; H, 3.99; Cl, 15.73; N, 12.29.

Method 2

A suspension of N-methyl-4-nitroaniline (20.0 g; 0.131 mol) in ethyl acetate (20 ml) is heated to 60° C. Within 15 min, a solution of chloro acetic anhydride (26.0 g; 0.151 mol) in ethyl acetate (60 ml) is added to this suspension. The resulting solution is then refluxed for 1 h, cooled to 75° C. and methyl cyclohexane (80 ml) is added. After seeding at 60° C., the suspension is further cooled down to 0° C. and stirred for an additional 1 h. The reaction mixture is filtrated, washed with methyl cyclohexane (40 ml) and the precipitate is dried to afford 25.9 g (83.3%) of the "chloroacetyl" compound as grey crystals.

EXAMPLE 6

Synthesis of the "Nitroaniline" (N-(4-nitrophenyl)-N-methyl-2-(4-methylpiperazin-1-yl)acetamide) and of the "Aniline" (N-(4-aminophenyl)-N-methyl-2-(4-methylpiperazin-1-yl)acetamide)

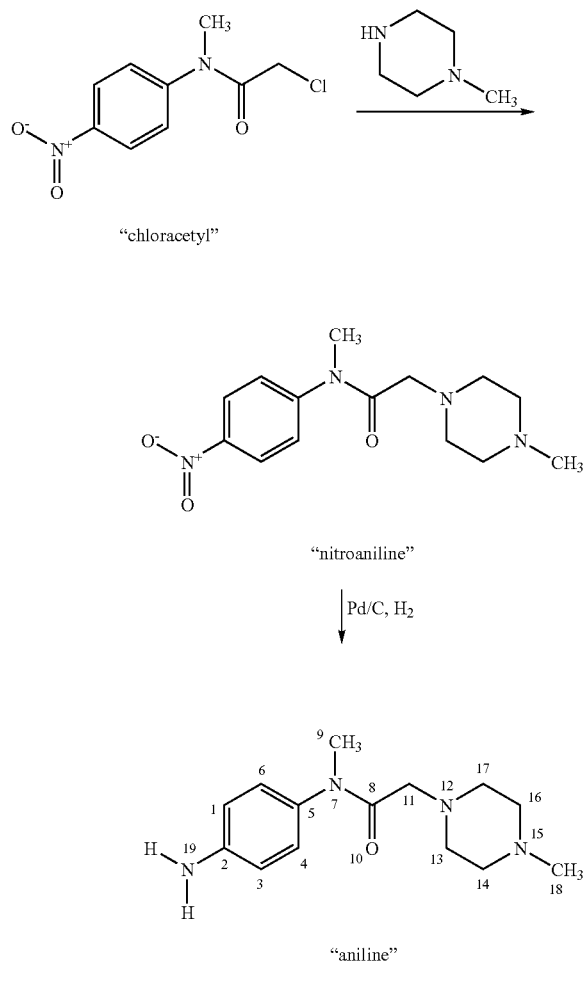

Method 1

A suspension of N-(4-nitroanilino)-N-methyl-2-chloroacetamide (20.0 g; 0.087 mol) in toluene (110 ml) is heated to 40° C. Within 30 min, 1-methylpiperazine (21.9 g; 0.216 mol) is added dropwise. After purging of the dropping funnel with toluene (5 ml) the reaction mixture is stirred for 2 h at 55° C., cooled to ambient temperature and washed with water (15 ml). The organic layer is diluted with isopropanol (100 ml) and Pd/C (10%; 1.0 g) is added. After subsequent hydrogenation ($H_2$, 4 bar) at 20° C. the catalyst is removed. Approximately 4/5 of the volume of the resulting solution is evaporated at 50° C. The remaining residue is dissolved in ethyl acetate (20 ml) and toluene (147 ml) heated to 80° C., then cooled to 55° C. and seeded. The reaction mixture is further cooled to 0° C. and stirred for 3 h at the same temperature. After filtration, the solid is washed with ice cold toluene (40 ml) and dried to afford 20.2 g (88.0%) of the "aniline" compound as white crystals. $^1$H-NMR (500 MHz, DMSO-$d_6$) δ: 6.90 (d, J=8.5 Hz, 1 H, 4-H+6-H); 6.65 (d, J=8.5 Hz, 1 H, 1-H+3-H); 5.22 (1 H, 19-$H_2$); 3.04 (s, 1 H, 9-$H_3$); 2.79 (s, 1 H, 11-$H_2$); 2.32 (m, 1 H, 13-$H_2$+17-$H_2$); 2.23 (m, 1 H, 14-$H_2$+16-$H_2$); 2.10 (s, 1 H, 18-$H_3$). $^{13}$C-NMR (126 MHz, DMSO-$d_6$) δ: 114.0 (C-1+C-3); 148.0 (C-2); 127.6 (C-4+C-6); 131.5 (C-5); 168.9 (C-8); 36.9 (C-9); 58.5 (C-11); 52.4 (C-13+C-17); 54.6 (C-14+C-16); 45.7 (C-18). MS (m/z): 263 (M+H)$^+$. Anal. calcd. for $C_{14}H_{22}N_4O$: C, 64.09; H, 8.45; N, 21.36. Found: C, 64.05; H, 8.43; N, 21.39.

Method 2

A suspension of N-(4-nitroanilino)-N-methyl-2-chloroacetamide (14.5 g; 0.063 mol) in ethyl acetate (65 ml) is heated to 40° C. Within 30 min, 1-methylpiperazine (15.8 g; 0.156 mol) is added dropwise. After purging of the dropping funnel with ethyl acetate (7 ml) the reaction mixture is stirred at 50° C. for 90 min, cooled to ambient temperature and washed with water (7 ml). The organic layer is diluted with isopropanol (75 ml) and dried over sodium sulphate. After separation of the solid, Pd/C (10%; 2.0 g) is added and the solution is hydrogenated ($H_2$, 5 bar) at ambient temperature without cooling. Subsequently the catalyst is removed by filtration and the solvent is evaporated at 60° C. The remaining residue is dissolved in ethyl acetate (250 ml) and recrystallized. After filtration and drying 10.4 g (60.4%) of the "aniline" compound are isolated as white crystals.

EXAMPLE 7

Synthesis of the "Anilino" (3-Z-[1-(4-(N-((4-methyl-piperazin-1-yl)-methylcarbonyl)-N-methyl-amino)-anilino)-1-phenyl-methylene]-6-methoxycarbonyl-2-indolinone)

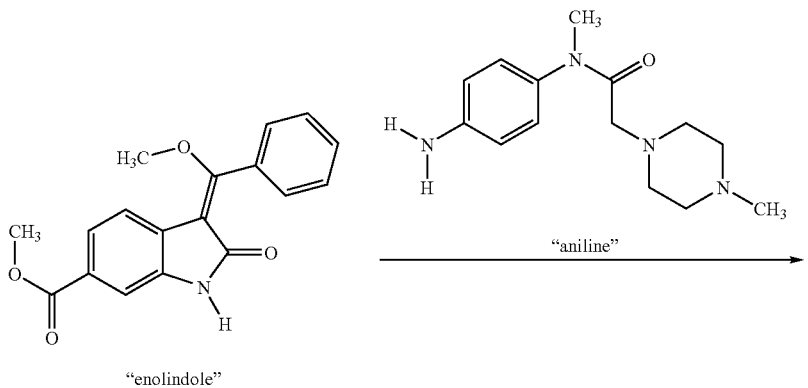

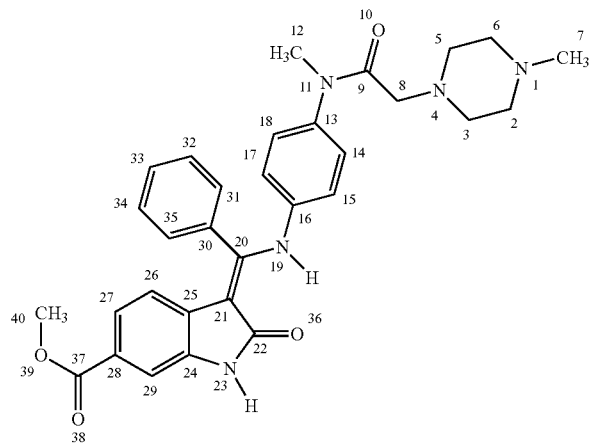

"anilino"

Method 1

A suspension of methyl-3-[methoxy(phenyl)methylene]-2-oxoindoline-6-carboxylate (10.0 g; 0.032 mol) and N-(4-aminophenyl)-N-methyl-2-(4-methylpiperazin-1-yl)acetamide (8.6 g; 0.032 mol) in a mixture of methanol (72 ml) and N,N-dimethylformamide (18 ml) is heated to reflux. After 7 h of refluxing the suspension is cooled down to 0° C. and stirring is maintained for additional 2 h. The solid is filtered, washed with methanol (40 ml) and dried to afford 15.4 g (88.1%) of the "anilino" compound as yellow crystals. $^{1}$H-NMR (500 MHz, DMSO-$d_6$) δ: 11.00 (s, 1 H, 23-H); 12.23 (s, 19-H); 7.61 (t; J=7.1 Hz, 1 H, 33-H); 7.57 (t, J=7.5 Hz, 1 H, 32-H+34-H); 7.50 (d, J=7.7 Hz, 1 H, 31-H+35-H); 7.43 (d, J=1.6 Hz, 1 H, 29-H); 7.20 (dd, J=8.3; 1.6 Hz, 1 H, 27-H); 7.13 (d, J=8.3 Hz, 1 H, 14-H+18-H); 6.89 (d, 8.3 Hz, 1 H, 15-H+17-H); 5.84 (d, J=8.3 Hz, 1 H, 26-H); 3.77 (s, 1 H, 40-$H_3$); 3.06 (m, 1 H, 12-$H_3$); 2.70 (m, 2H, 8-$H_2$); 2.19 (m, 1 H, 2-$H_2$, 3-$H_2$, 5-$H_2$, 6-$H_2$); 2.11 (s, 1 H, 7-$H_3$). $^{13}$C-NMR (126 MHz, DMSO-$d_6$) δ: 54.5 (C-2+C-6); 52.2 (C-3+C-5); 45.6 (C-7); 59.1 (C-8); 168.5 (C-9); 36.6 (C-12); 140.1 (C-13); 127.6 (C-14+C-18); 123.8 (C-17+C-15); 137.0 (C-16); 158.3 (C-20); 97.5 (C-21); 170.1 (C-22); 136.2 (C-24); 128.9 (C-25); 117.2 (C-26); 121.4 (C-27); 124.0 (C-28); 109.4 (C-29); 131.9 (C-30); 128.4 (C-31+C-35); 129.4 (C-32+C-34); 130.4 (C-33); 166.3 (C-37); 51.7 (C-40). MS (m/z): 540 (M+H)$^{+}$. Anal. calcd. for $C_{31}H_{33}N_5O_4$: C, 69.00; H, 6.16; N, 12.98. Found: C, 68.05; H, 6.21; N, 12.81.

Method 2

A suspension of methyl-3-[methoxy(phenyl)methylene]-2-oxoindoline-6-carboxylate (20.0 g; 0.064 mol) and N-(4-aminophenyl)-N-methyl-2-(4-methylpiperazin-1-yl)acetamide (17.1 g; 0.065 mol) in methanol (180 ml) is heated to reflux for 7.5 h. The resulting suspension is cooled down to 10° C. within 1 h and stirring is maintained for an additional 1 h. After filtration, the solid is washed with ice cold methanol (80 ml) and dried to afford 31.0 g (89.0%) of the "anilino" compound as yellow crystals.

The invention claimed is:

1. A compound of formula

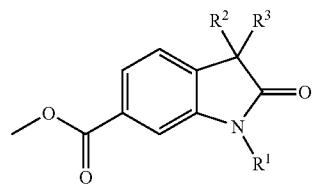

in which R$^1$ represents an hydrogen atom or a Cl—CH$_2$—CO-group, and R$^2$ and R$^3$ each represent an hydrogen atom or R$^2$ and R$^3$ taken together represent a

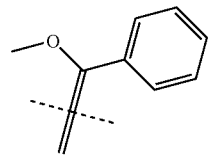

group, with the proviso that when R$^1$ represents an hydrogen atom R$^2$ and R$^3$ taken together represent a

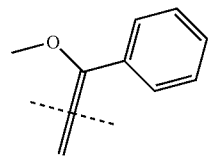

group.

2. A compound of formula

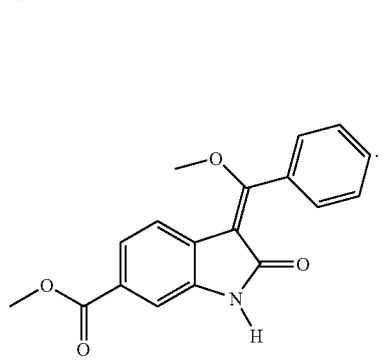

3. A compound of formula

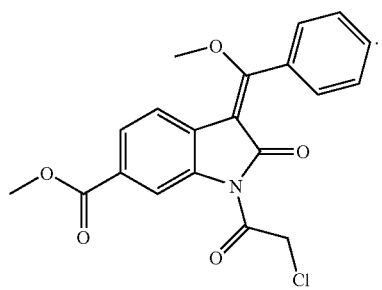

4. A compound of formula

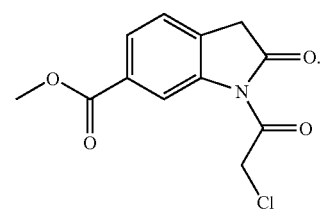

5. Process for the manufacture of a compound of formula

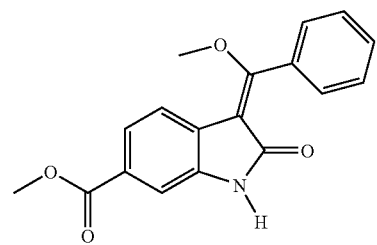

which comprises the step of base catalyzed dechloroacetylation of a compound of formula

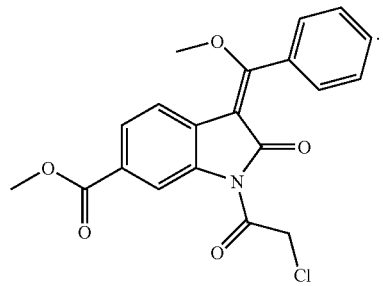

6. Process in accordance with claim 5, in which the compound of formula

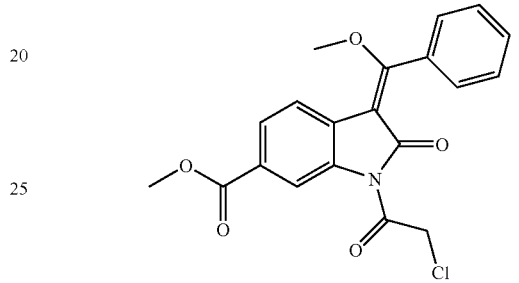

is obtained by reacting a compound of formula

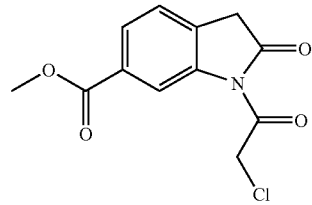

with a compound of formula

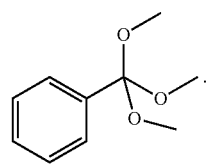

7. Process in accordance with claim 6, in which the compound of formula

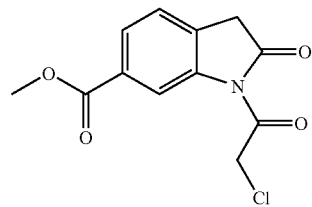

is obtained by reacting a compound of formula

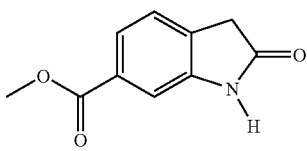

with a compound of formula

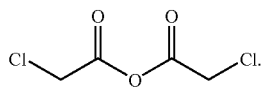

8. Process in accordance with claim 7, in which the compound of formula

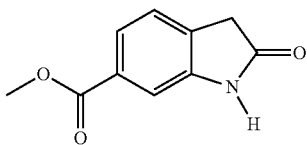

is obtained by the following steps:
(i) esterification of a compound of formula

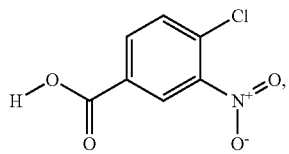

to obtain a compound of formula

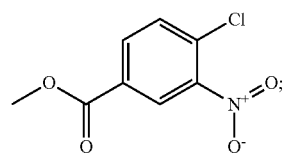

(ii) reacting the product of the reaction (i) with malonic acid dimethylester, to obtain a compound of formula

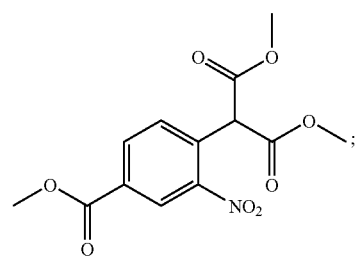

(iii) performing a cyclisation of the product of the reaction (ii) by a reaction of hydrogenation.

9. Process for the manufacture of a compound of formula

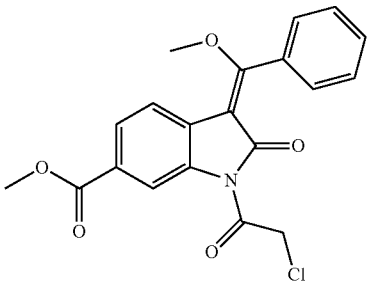

comprising the step of reacting a compound of formula

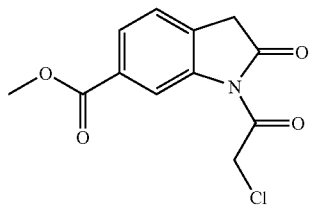

with a compound of formula

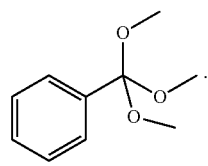

10. Process for the manufacture of a compound of formula

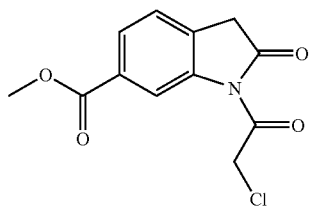

comprising the step of reacting a compound of formula

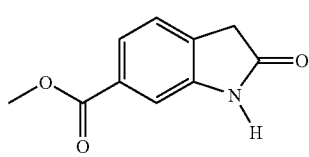

with a compound of formula

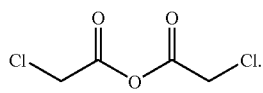

* * * * *